United States Patent [19]

Weber

[11] 4,285,885
[45] Aug. 25, 1981

[54] NOVEL DISTYRYLBENZENE CONTAINING SULFONIC ACID GROUPS

[75] Inventor: Kurt Weber, Basel, Switzerland

[73] Assignee: Ciba-Geigy Corporation, Ardsley, N.Y.

[21] Appl. No.: 110,274

[22] Filed: Jan. 7, 1980

[30] Foreign Application Priority Data

Jan. 17, 1979 [CH] Switzerland .......................... 439/79

[51] Int. Cl.³ .................. C07C 143/24; D06P 1/38; C09K 11/06
[52] U.S. Cl. .................. 260/505 R; 8/648; 252/301.21
[58] Field of Search .................. 260/505 C, 505 R; 8/648

[56] References Cited

U.S. PATENT DOCUMENTS

| | | | |
|---|---|---|---|
| 3,904,678 | 9/1975 | Schevermann et al. | 260/505 R |
| 3,984,399 | 10/1976 | Weber et al. | 260/505 R |

*Primary Examiner*—Alan Siegel
*Attorney, Agent, or Firm*—Edward McC. Roberts; John P. Spitals

[57] ABSTRACT

The bis-styrylbenzene of the formula

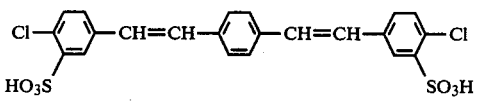

and the alkali metal, alkaline earth metal, ammonium and amine salts thereof, a process for its production and a method of whitening organic material which comprises the use of this compound.

3 Claims, No Drawings

NOVEL DISTYRYLBENZENE CONTAINING SULFONIC ACID GROUPS

The present invention relates to a novel distyrylbenzene containing sulfonic acid groups. A number of different distyrylbenzene compounds which contain sulfonic acid groups are already known, e.g. the compound disclosed in U.S. Pat. No. 3,904,678.

Surprisingly, it has now been found that a novel distyrylbenzene which contains sulfonic acid groups produces especially good white effects.

Accordingly, the present invention provides the distyrylbenzene of the formula

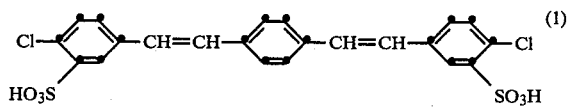

and the salts thereof.

Preferred salts are in general alkaline earth metal salts, e.g. calcium, barium or magnesium salts, and especially alkali metal salts, e.g. sodium or potassium salts, and also ammonium or amine salts.

The novel compound is advantageously obtained by reacting 1 mole of a compound of the formula

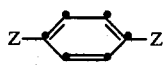

wherein Z is the grouping

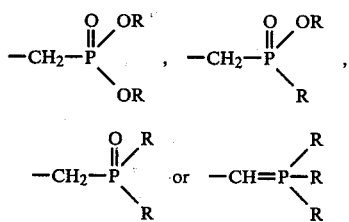

wherein R is an unsubstituted or substituted alkyl radical, an aryl radical, a cycloalkyl radical or an aralkyl radical, with 2 moles of the compound of the formula

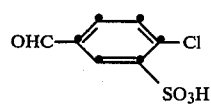

or of an alkali metal, ammonium or amine salt thereof, and, if desired, converting the resultant compound, in a manner known per se, into the free acid or the alkali metal, alkaline earth metal, ammonium and amine salts thereof.

The novel compounds defined above exhibit a more or less pronounced fluorescence in the dissolved or finely divided state. They can be used for whitening and/or brightening a wide variety of synthetic, regenerated man-made or natural organic materials or substances which contain such organic materials.

Without any restriction being implied by the following classification, examples of organic materials which can be treated with fluorescent whitening agents are:

I. Man-made organic material of high molecular weight:

(a) polymerisation products based on organic compounds containing at least one polymerisable carbon-carbon double bond, that is to say their homopolymers of copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compounds, for example acrylates, acrylic acid, acrylonitrile, acrylamides and their methacrylic analogues, of olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and and analogues, polycarbonates and silicones;

(d) polyadducts, such as polyurethanes (crosslinked and uncrosslinked) and epoxide resins.

II. Regenerated man-made organic material, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic material of animal or vegetable origin, for example based on cellulose or proteins, such as cotton, wool, linen, silk, natural film-forming resins, starch and casein.

The organic material to be whitened and/or brightened can be in the most diverse states of processing (raw materials, semi-finished goods or finished goods). On the other hand, it can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations or predominantly one dimensional bodies, such as filaments, fibres, flocks and wires. The above materials can, on the other hand, also be in an unshaped state, in the most diverse homogeneous or inhomogeneous forms of division, as for example in the form of powders, solutions, emulsions, dispersions, lattices, pastes or waxes.

Fibrous material can be, for example, in the form of endless filaments (stretched or unstretched), staple fibres, flocks, hanks, textile filament yarns, threads, nonwovens, felts, waddings, flocked structures or woven textile or bonded textile fabrics, knitted fabrics, and papers, cardboards or paper pulps.

The compounds to be used according to the invention are of importance, inter alia, for the treatment of organic textile material, especially woven textile fabrics. If fibres which can be in the form of staple fibres or endless filaments or in the form of hanks, woven fabrics, knitted fabrics, fleeces, flocked substrates or bonded fabrics, are to be whitened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of fluorescent whitening agent used, it can be advantageous to carry out the treatment in a neutral or alkaline or acid bath. The treatment is usually carried out in the temperature range from 20° to 140° C., for example at the boiling point of the bath or near it (about 90° C.).

Solutions or emulsions in organic solvents can also be used for the finishing according to the invention of textile substrates, as is practised in the dyeing industry in so-called solvent dyeing (pad-thermofixation application, or exhaust dyeing methods in dyeing machines). The fluorescent whitening agents of the present invention can further be added to, or incorporated in, the materials before or during their shaping.

If man-made or regenerated man-made organic materials are formed by spinning processes or from spinning solutions/melts, the fluorescent whitening agents can be applied by the following methods:

addition to the starting materials (for example monomers) or intermediates (for example precondensates or prepolymers), that is to say before or during the polymerisation, polycondensation or polyaddition, sprinkling in powder form on polymer chips or granules for spinning solutions/melts;

bath dyeing of polymer chips or granules for spinning solutions/melts;

metered addition to spinning melts or spinning solutions; and application to the spun tow before stretching.

The fluorescent whitening agents of the present invention can also be employed e.g. in the following formulations:

(a) in mixtures with dyes (shading) or pigments (coloured pigments or especially, for example, white pigments), or as an additive to dyebaths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilizers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft handle finishes, anti-soiling finishes or antistatic finishes, or antimicrobial finishes;

(d) incorporation of the fluorescent whitening agent in polymeric carriers (polymerisation, polycondensation or polyaddition products, in a dissolved or dispersed form, for use e.g. in coating agents, impregnating agents or binders (solutions, dispersions and emulsions) for textiles, nonwovens, papers and leather;

(e) as additives to master batches;

(f) as additives to a wide variety of industrial products in order to render these more marketable (for example improving the appearance of soaps, detergents, pigments);

(g) in combination with other substances having fluorescent whitening properties;

(h) in spinning bath preparations, that is to say as additives to spinning baths which are used for improving the slip for the further processing of synthetic fibres, or from a special bath before the stretching of the fibre;

(i) as scintillations for various purposes of a photographic nature, for example for electrophotographic reproduction or supersensitising;

(j) depending on the substitution, as laser dyes.

If the whitening process is combined with textile treatment or finishing methods, the combined treatment can in many cases advantageously be carried out with the aid of appropriate stable preparations which contain the fluorescent whitener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example in the range from at least 60° C. to about 130° C. The heat treatment in the dry state is then advantageously carried out at a temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferable to use amounts between 0.0005 and 0.5 percent by weight.

For various reasons it is often advantageous not to use the fluroescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent whitening agents of this invention are also particularly suitable for use as additive for wash liquors or heavy duty and domestic detergents, to which they can be added in various ways. They are advantageously added to wash liquors in the form of their solutions in water or organic solvents, or, in finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry powder. For example, the whitening agents can be mixed, kneaded or ground with the surface-active substances and, in this form, admixed with the finished powder. However, they can also be sprayed in a dissolved or pre-dispersed form on the finished detergent.

Suitable detergents are the known mixtures of active detergents, for example soap in the form of chips and powders, synthetics, soluble salts of sulfonic acid hemi-esters of higher fatty alcohols, arylsulfonic acids with higher and/or multiple alkyl substituents, sulfocarboxylic acid esters of medium to higher alcohols, fatty acid acylaminoalkyl- or acylaminoaryl-glycerol sulfonates and phosphoric acid esters of fatty alcohols. Suitable builders which can be used are, for example, alkali metal polyphosphates and polymetaphosphates, alkali metal pyrophosphates, alkali metal salts of carboxymethyl cellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The novel fluorescent whitening agents have the particular advantage that they are also active in the presence of active chlorine donors, for example, hypochlorite, and can be used without significant loss of effect in wash liquors containing non-ionic washing agents, for example alkylphenolpolyglycol ethers.

The compounds of the invention are added in amounts of 0.005 to 1% or more, based on the weight of the liquid or powdered finished detergent. Wash liquors which contain the indicated amounts of the claimed fluorescent whitening agents impart a brilliant appearance in daylight when used to wash textiles made from cellulose fibres, polyamide fibres, cellulose fibres with a high quality finish, polyester fibres or wool.

The washing treatment is carried out e.g. as follows: The textiles are treated for 1 to 30 minutes at 20° to 100° C. in a wash liquor which contains 1 to 10 g/kg of a built-up composite detergent and 0.05 to 1%, based on the weight of the detergent, of the fluorescent whitening agent. The liquor ratio can be 1:3 to 1:50. After they have been washed, the textiles are rinsed and dried in the usual manner.

The wash liquor can contain 0.2 g/l of active chlorine (for example in the form of hypochlorite) or 0.1 go 2 g/l of sodium perborate.

In the following Examples, percentages are always by weight.

EXAMPLE 1

18.9 g of p-xylylene-diphosphonic acid tetraethyl ester and 25.2 g of the sodium salt of 4-chlorobenzaldehyde-3-sulfonic acid (content: 96%) are dissolved at 40° C. in 200 ml of dimethyl sulfoxide with expulsion of air. Then 7.2 g of sodium methylate (content: 97.3%) are added at 40°–45° C. in the course of 20 minutes, and the mixture is stirred for 4 hours at the same temperature. While cooling, 100 ml of desalinated water are then added. The crystalline product is collected by filtration at 15° C., washed with 100 ml of desalinated water and recrystallised twice from 2000 ml and 1500 ml of water and dried in vacuo at 85° C., affording 15.3 g of the compound of the formula

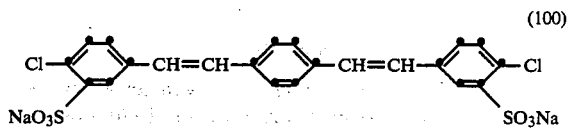
(100)

in the form of a pale yellow powder. UV spectrum: $\lambda_{max}$ 363 nm, measured in dimethyl formamide/water (1:1).

Instead of using p-xylylene-diphosphonic acid tetraethyl ester, it is also possible to use the equivalent amount of p-xylylene-diphosphonic acid tetramethyl ester. Likewise, it is possible to use dimethyl formamide instead of dimethyl sulfoxide and an approx. 30% sodium methylate solution instead of solid sodium methylate. Finally, sodium hydroxide or potassium hydroxide powder can also be used as alkaline condensation agent.

The respective barium or calcium salt is obtained by dissolving the compound of the formula (1) in water and adding barium or calcium chloride.

The compound of the formula (1) is obtained in the form of the free sulfonic acid by passing the aqueous solution of the compound of the formula (1) through a column which contains a strongly acid ion exchanger and then evaporating the acid solution to dryness. The compounds listed in the following table can be obtained by neutralising the aqueous solution of the free sulfonic acid with equimolar amounts of the corresponding base:

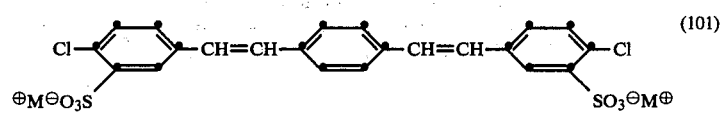
(101)

TABLE

| Compound | $M^{\oplus}$ |
|---|---|
| 102 | K |
| 103 | $NH_4$ |
| 104 | $HN(CH_2CH_2OH)_3$ |
| 105 | 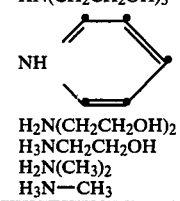 NH |
| 106 | $H_2N(CH_2CH_2OH)_2$ |
| 107 | $H_3NCH_2CH_2OH$ |
| 108 | $H_2N(CH_3)_2$ |
| 109 | $H_3N-CH_3$ |

EXAMPLE 2

Polyamide 66 woven jersey fabric is treated in a dyeing machine with an aqueous bath of the following composition: 0.5% of the compound of the formula (100), based on the weight of the goods, and 3 g/l of sodium dithionite ($Na_2S_2O_4.2H_2O$) stabilised with sodium pyrophosphate ($Na_2P_2O_7$) and 1 ml/l of 80% acetic acid. The liquor ratio is 1:30.

Treatment is effected in accordance with the following temperature programme:
  40° C. to 97° C. in the course of 30 minutes
  97° C. in the course of 30 minutes, and
  97° C. to 40° C. in the course of 15 minutes.

The goods are given an aftertreatment by rinsing them for 30 seconds in running dionised water. After it has been dried, the polyamide 66 woven jersey fabric has an excellent white effect.

EXAMPLE 3

A (non-fixed) polyamide 66 woven jersey fabric is padded at room temperature with the following aqueous liquor:
  4 g/l of the compound of the formula (100),
  16 g/l of urea,
  15 g/l of polyoxyethylene with a molecular weight of 600,
  5 ml/l of 80% acetic acid.

The pick-up is 100%. The goods are thermofixed for 30 seconds at 180° C. The treated jersey fabric has an excellent white effect.

EXAMPLE 4

A cotton fabric is treated in a dyeing machine with an aqueous bath of the following composition:
  0.2 g of the compound of the formula (100),
  5 g/l of crystalline sodium sulfate (addition after 15 minutes). The liquor ratio is 1:30.

Treatment is effected in accordance with the following temperature programme:
  20° C. to 50° C. in the course of 15 minutes
  50° C. in the course of 15 minutes.

The fabric is given an aftertreatment by rinsing it for 30 seconds in running deionised water. After is has been dried, the cotton fabric has an excellent white effect.

EXAMPLE 5

Cotton fabric is padded at room temperature with an aqueous liquor which contains 2 g/l of the compound of the formula (100). The pick-up is 75%. The cotton is then dried for 60 seconds at 130° C. The treated cotton fabric has an excellent white effect.

EXAMPLE 6

Cotton textile material is washed for 15 minutes in a warm liquor of 60° C. which contains 4 g/l of a washing powder of the following composition:

| | |
|---|---|
| compound of the formula (100) | 0.8% |
| alkylarylsulfonate | 15.7% |
| fatty alcohol sulfonate | 3.7% |
| coconut fatty acid monoethanolamide | 2.7% |
| sodium tripolyphosphate | 39.0% |
| sodium silicate | 4.0% |
| magnesium silicate | 2.0% |
| carboxymethyl cellulose | 1.0% |
| sodium ethylenediaminetetraacetate | 0.5% |
| sodium sulfate and water to make up | 100.0% |

The liquor ratio is 1:20.

After it has been rinsed and dried, the cotton has an attractive white effect.

What is claimed is:

1. The bis-styrylbenzene of the formula

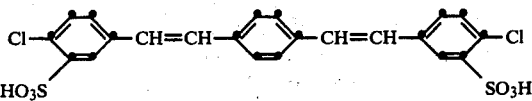

and the alkali metal, alkaline earth metal, ammonium and amine salts thereof.

2. The bis-styrylbenzene according to claim 1 of the formula

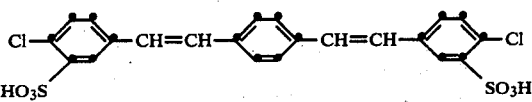

and the sodium and potassium salts thereof.

3. The bis-styrylbenzene according to claim 2 of the formula

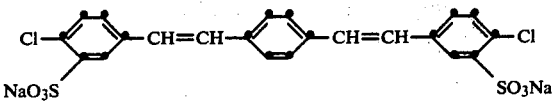

* * * * *